(12) United States Patent
Gleich et al.

(10) Patent No.: US 12,390,199 B2
(45) Date of Patent: Aug. 19, 2025

(54) MICRODEVICE AND REGISTRATION APPARATUS

(71) Applicant: KONINKLIJKE PHILIPS N.V., Eindhoven (NL)

(72) Inventors: Bernhard Gleich, Hamburg (DE); Juergen Erwin Rahmer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 62 days.

(21) Appl. No.: 18/073,816

(22) Filed: Dec. 2, 2022

(65) Prior Publication Data
US 2024/0115243 A1 Apr. 11, 2024

Related U.S. Application Data

(60) Provisional application No. 63/414,000, filed on Oct. 7, 2022.

(51) Int. Cl.
*A61B 8/00* (2006.01)
*A61B 5/06* (2006.01)
*A61B 8/08* (2006.01)

(52) U.S. Cl.
CPC ............ *A61B 8/5261* (2013.01); *A61B 5/062* (2013.01); *A61B 8/0841* (2013.01); *A61B 8/4416* (2013.01); *A61B 2562/0247* (2013.01)

(58) Field of Classification Search
CPC ..... A61B 5/062; A61B 8/0841; A61B 8/5261; A61B 8/4416; A61B 2562/0247
See application file for complete search history.

(56) References Cited

U.S. PATENT DOCUMENTS

| | | | | |
|---|---|---|---|---|
| 5,619,997 A | * | 4/1997 | Kaplan | A61B 5/0031 73/54.41 |
| 2013/0296691 A1 | | 11/2013 | Ashe | |
| 2015/0265171 A1 | * | 9/2015 | Seaver | A61B 5/0002 600/561 |
| 2016/0374643 A1 | | 12/2016 | Halmann | |

(Continued)

FOREIGN PATENT DOCUMENTS

WO WO2012025854 A1 3/2012

OTHER PUBLICATIONS

PCT International Search Report, International application No. PCT/EP2023/077030, Feb. 26, 2024.

*Primary Examiner* — Chao Sheng

(57) ABSTRACT

Disclosed in some embodiments are microdevices, medical devices and a registration apparatuses that allow for tracking of medical device(s) in an ultrasound image while maintaining the quality of the ultrasound image. The microdevice comprises a casing and a magneto mechanical resonator. The magneto mechanical resonator comprises at least two magnetic objects providing a permanent magnetic moment. The magneto mechanical resonator is adapted to transduce an external excitation field into a mechanical movement of the at least two magnetic objects relative to each other such that a changing magnetic response field is generated. A pressure sensor is arranged such that an external ultrasound signal induces an additional movement of the magnetic objects such that the changing magnetic response field is changed in dependency of the external ultrasound signal.

17 Claims, 4 Drawing Sheets

(56) References Cited

U.S. PATENT DOCUMENTS

| | | |
|---|---|---|
| 2018/0296185 A1 | 10/2018 | Cox |
| 2020/0397530 A1 | 12/2020 | Gleich |
| 2021/0244305 A1* | 8/2021 | Gleich ............... A61B 5/02152 |
| 2022/0071506 A1 | 3/2022 | Dirksen |
| 2022/0175487 A1 | 6/2022 | Gleich |
| 2022/0257138 A1 | 8/2022 | Gleich |

* cited by examiner

MICRODEVICE AND REGISTRATION APPARATUS

FIELD

The present disclosure is directed, in general, to the field of microdevices for insertion into a human body, reading systems for reading a signal from microdevice(s), and methods related thereto. Further, the present disclosure is also directed, in general, to the field of registration apparatuses, methods and computer programs for registering ultrasound system(s) with an electromagnetic reading system(s) for reading a signal from the microdevice.

BACKGROUND

In medical proceedings it is often important to determine a position of a medical device within a region of interest. In particular, a lot of medical procedures utilize ultrasound to image a region of interest and to perform a surgical procedure using a medical device under ultrasound guidance. However, the medical devices themselves are often poorly visible in the ultrasound image. This shortcoming can make the performance of procedures that depend on the precise movement of a medical device within the region of interest difficult and cumbersome to perform.

Generally, marker devices for marking the medical device that are visible in ultrasound are known and can be utilized to visualize the medical device in the ultrasound image. However, markers which are visible in ultrasound, in particular, reflect respective ultrasound signals, can often lead to distortions and imaging artifacts that do lead to a decrease in the image quality of the ultrasound image.

SUMMARY

Various embodiments provide a microdevice, a reading system for reading a signal from the microdevice, a registration apparatus, a registration method and a computer program product that allow for tracking a device in an ultrasound image while maintaining the quality of the ultrasound image.

Some embodiments include a microdevice for insertion into a human body. The microdevice comprises a casing and within the casing a magneto mechanical resonator. The magneto mechanical resonator comprises: at least two magnetic objects providing a permanent magnetic moment. The magneto mechanical resonator (in response to an external magnetic or electromagnetic excitation field) transduces the external magnetic or electromagnetic excitation field into a mechanical movement of the at least two magnetic objects relative to each other such that a changing magnetic response field is generated. The microdevice further comprises a pressure sensor responsive to an external ultrasound signal.

Some embodiments include a microdevice for insertion into a human body are presented, wherein the microdevice allows for measuring a location of the microdevice in space, wherein the microdevice comprises a casing and within the casing a magneto mechanical resonator, wherein the magneto mechanical resonator comprises a) at least two magnetic objects providing a permanent magnetic moment, wherein the magneto mechanical resonator is adapted to transduce an external magnetic or electromagnetic excitation field into a mechanical movement of the at least two magnetic objects relative to each other such that a periodically changing magnetic response field is generated, and b) a pressure sensor arranged such that an external ultrasound signal induces an additional movement of the magnetic objects such that the periodically changing magnetic response field is changed in dependency of the external ultrasound signal.

Since the microdevice comprises a pressure sensor arranged such that an external ultrasound signal induces an additional movement of the magnetic objects such that the periodically changing magnetic response field is changed in dependency of the external ultrasound signal, it is not only possible to determine a location of the microdevice using an electromagnetic reading system but also to determine when an ultrasound signal is transmitted in the direction of the microdevice. This allows to determine a registration between the electromagnetic reading system of a microdevice and the ultrasound system such that the location determined for the microdevice can be integrated into the ultrasound image very accurately. Moreover, the microdevice is small enough to be integrated into any medical tool and thus allows to determine the position of the medical tool in the ultrasound image. Furthermore, since the microdevice only passively detects the ultrasound signal and changes the electromagnetic signal transmitted by the microdevice instead of changing the ultrasound signal itself, the ultrasound signal and thus the ultrasound image are not affected by the presence of the microdevice. Thus, the microdevice allows to track the position of the medical tool in an ultrasound image without affecting the ultrasound image.

Generally, microdevices refer to devices that are smaller than 1 millimeter in at least one spatial direction. In some embodiments, the microdevice is smaller than 1 millimeter in at least two orthogonal spatial directions. The microdevice may be smaller than 1 millimeter in all spatial directions, i.e. in each spatial direction. In an embodiment, the microdevice comprises a size that allows it to be introduced into a circulatory system or a cavity in the body of a human being. However, even smaller sizes or larger sizes are possible for the microdevice.

The casing can be any casing surrounding the magneto mechanical resonator and can be adapted in accordance with a specific application of the microdevice. The casing can comprise a coating referring in particular to a biocompatible coating. Moreover, the casing can be provided as part of a medical device into which the microdevice is integrated. For example, a part of the casing of the medical device or tool can form at least a part of the casing of the microdevice. Generally, the casing is adapted to transmit the ultrasound signals such that the pressure sensor can react to the pressure difference caused by the external ultrasound signal. For example, the casing can be provided with openings or flexible parts that allows to transmit a pressure difference caused by an ultrasound signal to interact with the pressure sensor. Moreover, the pressure sensor can be arranged in contact or as part of the casing such that the ultrasound signal can directly influence the pressure sensor.

The at least two magnetic objects providing a permanent magnetic moment are beneficially made of a hard magnetic material allowing to keep a once introduced magnetic moment. The magnetic objects refer to neodymium magnets with a high remanence of N52, i.e. of 1.42 T. In applications in environments with a temperature of more than 80° C., for instance during ablation procedures, it is noted that the magnetic object refers to a neodymium magnet with H, SH, EH or AH characteristics according to the general neodymium magnet identification system. Also CoSm (cobalt samarium) magnets can be employed as magnetic objects.

In some embodiments, the magnetic objects comprise a spherical shape that can improve a reliability of the microdevice. However, the magnetic object can also be provided in other shapes, for instance, in a cylindrical shape. Moreover, the magnetic objects can have two different shapes, for example, one magnetic object can comprise a spherical shape while another magnetic object can comprise a cylindrical shape.

The magneto mechanical resonator is adapted to transduce an external magnetic or electromagnetic field into a mechanical movement of the least two magnetic objects relative to each other. In particular, the external magnetic or electromagnetic excitation field refers to an oscillating field comprising a constant or a chirped frequency for exciting the mechanical movement of the at least two magnetic objects with respect to each other. The mechanical movement can refer to any movement that moves at least one of the magnetic objects with respect to the other magnetic objects. For example, the mechanical movement can refer to a rotation of a magnetic object relative to other magnetic objects or to a linear movement away or towards other magnetic objects. In some embodiments, one of the least two magnetic objects is arranged fixed with respect to the casing, for example, by fixedly attaching the magnetic object to the casing, whereas the other magnetic object is arranged such that it can move relative to the fixed magnetic object. In an example embodiment one of the at least two magnetic objects is arranged such that it provides a restoring force to another of the at least two magnetic objects if the other of the at least two magnetic objects deviates from an equilibrium position. In this case it is beneficial that the mechanical movement of the at least one of the at least two magnetic objects refers to a rotational movement and the restoring force refers to a restoring torque provided to the respective moving magnetic object. However, the restoring force can also be provided by a restoring force providing element like a spring attached to one of the at least two magnetic objects. Generally, the arrangement of the at least two magnetic objects in the magneto mechanical resonator causes a relative movement of the at least two magnetic objects that generates a periodically changing respond field. Based on the periodically changing magnetic respond field a respective readout system can utilize the external magnetic or electromagnetic excitation field and determine the location of the microdevice with respect to the readout system.

The magneto mechanical resonator further comprises a pressure sensor. The pressure sensor is arranged such that an external ultrasound signal induces an additional movement of the magnetic objects such the periodically changing magnetic response field is changed in dependency of the external ultrasound signal. Beneficially, the pressure sensor is arranged such that it causes a change in the distance between the at least two magnetic objects as additional movement of the magnetic objects. Since a change in the distance as additional movement changes the interaction between the two magnetic objects, also the periodically changing magnetic response field is changed depending on the external ultrasound signal. However, the pressure sensor can also be arranged such that it changes a rotation movement of the magnetic object, for instance, induces an additional rotation or hinders a rotation of at least one of the magnetic objects. Generally, the pressure sensor is sensitive to pressure. In some embodiments, the pressure sensor senses, for example, the pressure differences induced by an external ultrasound signal in the environment of the pressure sensor. In some embodiments, the pressure sensor is sensitive to the quadratic terms of the pressure field caused by the ultrasound, wherein the quadratic terms refer to a pushing force induced into the environment of the pressure sensor by the absorbed or reflected ultrasound energy. In particular, it is beneficial that the pressure sensor is configured to cause the additional movement when subjected to a pressure difference lower than 0.2 mbar, more beneficially lower than 0.05 mbar and even more beneficially lower than 0.01 mbar. Beneficially, the pressure sensor is arranged such that a frequency of the additional movement induced by the external ultrasound signal is smaller than a frequency of the ultrasound signal. In particular, the dominant Fourier component of the additional movement is a smaller frequency than the frequency of the ultrasound signal.

In an example embodiment the casing and the pressure sensor are configured such that the pressure difference caused by the external ultrasound signal at different parts of the casing causes the additive movement. Arranging the pressure sensor and configuring the casing such that a pressure difference at different parts of the casing causes the additional movement enables determination of the pressure difference on the respective parts of the casing. Since generally the pressure difference caused on different parts of a casing relates to the direction at which the external ultrasound signal meets the microdevice, the direction of the external ultrasound signal with respect to the microdevice orientation can be derived from a change in the magnetic response field caused by the additional movement. Thus, this embodiment allows not only to determine when an ultrasound signal meets the microdevice but also from which direction the ultrasound signal is coming with respect to the orientation of the microdevice. Beneficially, in this embodiment, the casing comprises at least two openings, wherein the pressure sensor is arranged between the at least two openings such that the pressure sensor experiences at two opposing sides a pressure difference in the presence of an external ultrasound signal. Generally, the openings refer to parts of the casing that allow to transmit a pressure provided at the casing into an inner part of the casing. Thus, the openings can be completely free of any material and can provide a direct fluidic contact between the outsides and the insides of the casing. However, it is beneficial that the openings are provided with a flexible membrane that allows to transmit a pressure applied at a casing inside the casing without allowing a direct contact of the insides of the casing with the outsides of the casing. In an example embodiment four openings are provided, wherein two of the openings are provided on each side of the pressure sensor respectively. Providing four openings allows for an accurate and fast pressure adaptation of the inside pressure to the outside pressure cause by the ultrasound signal at the casing of the microdevice. Thus, the detection of the ultrasound signal and the direction of the ultrasound signal becomes even more accurate.

In an embodiment, the pressure sensor is a flexible membrane, and wherein one of the magnetic objects is attached to the flexible membrane such that a movement of the flexible membrane causes a movement of the magnetic object. In some embodiments, the flexible membrane is formed by a flexible material, in particular, a rubber material like latex or a silicone but allows for a fast and flexible movements of the flexible membrane in reaction to the applied pressure. Beneficially, the flexible membrane is configured to flex at pressures below 0.2 mbar, more beneficially, 0.05 mbar, even more beneficially, below 0.01 mbar. Generally, the magnetic object can be attached indirectly to the flexible membrane via any kind of attachment, for instance, by an attaching filament, a holding structure, a bearing, et cetera. Moreover, the magnetic object can also be directly attached to the flexible membrane, for example, by integrating the magnetic object into the flexible membrane. In case the magnetic object is directly attached to the flexible membrane, in particular, integrated into the flexible membrane, the magnetic object only moves with the movements of the flexible membrane such that it is further beneficial in this embodiment that the other magnetic object provides the movement that causes the magnetic response field, for example by rotating relative to the magnetic object attached to the membrane. The movement of the flexible membrane caused by the ultrasound signal then causes a change in the relative movement between the two magnetic objects leading to a change in the forces between the two magnetic object and thus to a changed response field. Thus, a movement of the flexible membrane causes in this embodiment a change in the periodically changing response field that depends on the external ultrasound signal.

Some embodiments of the present invention a medical device for use during a surgical procedure under ultrasound guidance comprising a microdevice as described above are presented. In some embodiments, the medical device comprises a tip adapted such as to have the microdevice attached thereto. In some embodiments, the medical device may comprise one or more of an interventional device or an implant, in particular an electrical implant and/or an orthopedic implant. In some embodiments, the medical device may particularly comprise one or more of: a surgical instrument, an imaging probe, an endoscope, a bronchoscope or an ingestible pill. Alternatively or additionally, the medical device may comprise one or more of a catheter, a wire, in particular a guidewire, a stent, one or more aneurism coilings, one or more vena cava filters, a heart valve, a shunt, a needle, a wire, a tube, a stylet or a radioactive seed. In some embodiments, the medical device may have a longitudinal shape. The medical device may be adapted to have a plurality of microdevices as described herein above attached thereto, wherein the plurality of microdevices may be arranged along longitudinal axis of said medical device.

In some embodiments, a registration apparatus for registering an ultrasound system with an electromagnetic reading system for reading a signal from a microdevice is presented. In such embodiments, the apparatus comprises i) a receiving interface configured to receive a) a signal indicative of a transmit direction of an external ultrasound signal transmitted by the ultrasound system and b) an electrical response signal of the microdevice provided by the microdevice in response to a magnetic or electromagnetic excitation field provided by the electromagnetic reading system, ii) a processor arranged to register the ultrasound system with the reading system based on the electrical response signal and the transmit direction.

Since the registration apparatus is arranged to register the ultrasound system with the reading system based on the electrical response signal of a microdevice that is arranged to sense the ultrasound signal of the ultrasound system and the transmit direction, the registration can be performed very accurately even when the marker device is within the human body, or in the presence of magnetic field disturbances.

The registration apparatus is arranged to register an ultrasound system with an electromagnetic reading system used for reading the signal from a microdevice as described above. Generally, the registration apparatus can be realized in form of any computing device, for example, by utilizing one or more processors for performing the functions of the registration apparatus. Moreover, the registration apparatus can also be realized in form of network computing, for example, utilizing cloud computing or other distributed computing techniques.

The registration apparatus comprises a receiving interface, wherein the receiving interface can be realized in any form of communicative interface for communicating with other computing devices, i.e. to receive wired and/or wireless data signals. In particular, the receiving interface is arranged to receive a) a signal indicative of a transmitted direction of an external ultrasound signal transmitted by the ultrasound system and b) an electric response signal of the microdevice provided by the microdevice in response to a magnetic or electromagnetic excitation field provided by the electromagnetic reading system. For example, the receiving interface can be arranged to be communicatively coupled with a memory on which the respective signals are already stored. However, the receiving interface can also be communicatively coupled directly to the ultrasound system and/or the electromagnetic reading system for receiving the respective signals directly from the systems providing these signals. The signals can be provided and received in form of any digital or analogue signal that allows to determine the information coded in the signal as defined above.

Generally, the ultrasound system can be any ultrasound system, for example a handheld ultrasound system or an automatic ultrasound system that is arranged to provide and transmit an ultrasound signal into a region of interest of a patient. An ultrasound system transmits an ultrasound signal into a distinct clearly defined region of the patient, for example, utilizing a fan beam, stencil beam or cone beam, wherein a region of interest is scanned by the ultrasound by repeatedly changing the direction into which the ultrasound signal in the region of interest is transmitted. Thus, providing the transmit direction with respect to a known point in space, for example, the region of interest or the position of the ultrasound transducer allows to clearly define the space covered by the ultrasound signal at any given time.

Generally, an electromagnetic reading system for reading a signal from a microdevice comprises one or more coils for generating and/or receiving electromagnetic fields. In particular, an electromagnetic reading system for reading a signal from a microdevice as described above comprises at least one coil that is arranged for providing the magnetic or electromagnetic excitation field for exciting the microdevice and one or more coils that are arranged for receiving the electrical response signal of the microdevice. The electrical response signal of the microdevice is generally indicative of the location of the microdevice for example, a direction of the electromagnetic excitation field and a response time of the electrical response signal can be utilized to determine the location of the microdevice. Moreover, if more than one coil is utilized by the reading system also a comparison of the electrical response signals received by each of the different coils allows to derive a location of the microdevice. Thus, the electrical response signal allows to determine a location of the microdevice very accurately. Moreover, since the microdevice as described above is arranged to provide an electrical response signal that changes with the presence of an ultrasound signal at the microdevice, it can also be determined very accurately based on the electrical response signal whether or not the microdevice is subjected at any given time to an ultrasound signal. Thus, based on the electrical response signal and the transmit direction of the ultrasound signal the processor can be configured to register the ultrasound system with the reading system. In this context the registration refers to determining a function that allows to transform a location of the microdevice determined in a coordinate system of the electromagnetic reading system into a location in the coordinate system of the ultrasound system. Thus, if the ultrasound system and the electromagnetic reading system are registered a location of the microdevice determined by the electromagnetic reading system is also directly known with respect to the ultrasound system. Accordingly, the location of the microdevice in the ultrasound image can be determined and provided to a user.

In an example embodiment the processor is further adapted to determine a presence or absence of an external ultrasound signal at the microdevice based on the response signal and a location of the microdevice relative to the electromagnetic reading system based on the response signals, and to register the ultrasound system with the reading system based on a transmit direction of the external ultrasound signal, the determined location and the determined presence or absence of the external ultrasound signal. Based on the determined location and based on the determined presence or absence of the external ultrasound signal it can be determined at which point in time the ultrasound signal is received by the microdevice and thus at which point in time the ultrasound signal is directed at the location of the microdevice. Moreover, since the location of the microdevice in the coordinate system of the reading system and the direction of the ultrasound signal in the coordinate system of the ultrasound system is known the two systems can be registered in at least one direction. Moreover, if the ultrasound signal refers to a stencil beam that covers substantially a line area in the region of interest the registration can also be performed in two directions. The further information with respect to the third coordinate can then be provided, for instance, based on respective pre-knowledge, for example, during a calibration procedure the distance between the ultrasound transducer and the microdevice can be predetermined or measured directly. The position of the ultrasound transducer in the coordinate system of the reading system is provided. For example, the position can be indicated by a user or during a calibration procedure the medical instrument comprising the marker in a known relative position in the instrument can be used to determine the position of the ultrasound system in the coordinate system of the reading system, for instance, by touching the medical instrument to a predetermined part of the ultrasound system. In an embodiment the ultrasound system can be configured to comprise an additional marker, wherein in this case the reading system is adapted to determine the location of the additional marker based on a signal of the additional marker, wherein the registration is then further based on the determined location of the additional marker. The additional marker allows for measuring a location of the additional maker in space. Since the additional marker is provided as part of the ultrasound system and not provided within the human body, the marker is not subjected to the same size restrictions as the microdevice. Thus the additional marker can be realized as any known marker that provides an electromagnetic signal in the presents of a changing electromagnetic field or can even be realized as an active electromagnetic source. For example, the marker can comprise an LC resonator or a sending coil. However, the additional marker can also be realized as an additional microdevice, wherein the additional microdevice also comprises a magneto mechanical resonator, wherein the magneto mechanical resonator comprises a) at least one magnetic object providing a permanent magnetic moment, wherein the magneto mechanical resonator is adapted to transduce an external magnetic or electromagnetic excitation field into a mechanical movement of the at least one magnetic object such that a periodically changing magnetic response field is generated. For example, the mechanical resonator of the additional microdevice can be similar to the mechanic resonator of the microdevice. However, in this embodiment it is not necessary that the additional microdevice comprises an ultrasound sensing possibility. Thus in the additional microdevice parts referring to this additional sensing possibility can be omitted. Based on the determined position of the additional marker on the ultrasound system the reading system can be registered in all three directions, in particular, during a calibration procedure in which the ultrasound system is positioned at different positions relative to the microdevice. However, in some embodiments it can also be suitable to register only in one or two directions. For example, if a coordinate of the third direction, in particular, a distance between the microdevice and the ultrasound system is determined and known due to the nature of the medical procedure or if an accurate location determination in one direction is not necessary for the success of the procedure. However, it is beneficial that the processor determines a distance between the source of the ultrasound signal provided by the ultrasound system and the microdevice based on the response signal, and to register the ultrasound system with the reading system further based on the determined distance. The distance between the source of the ultrasound signal and the microdevice can be determined based on the electrical response signal, for example, based on the strength of the parts of the response signal that indicate the presence of the ultrasound signal. Since the ultrasound signal strength also depends on the distance between the source and the microdevice, and since the response of the microdevice direct ultrasound signal also depends on the strength of the ultrasound signal reaching the microdevice, the distance between the microdevice and the ultrasound transducer can be determined. This allows for a registration in which a calibration step is omitted and the registration is directly performed with a microdevice placed in the region of interest.

Furthermore, to increase the accuracy of the registration, it is beneficial to use the processor to determine a direction of the ultrasound signal relative to the microdevice (e.g., determine the direction under which the ultrasound signal reaches the microdevice). Since the pressure differences caused in the pressure sensor of the microdevice can depend on the direction under which the ultrasound signal reaches the microdevice, the pressure sensor, the response signal is indicative also of the direction under which the ultrasound signal reaches the microdevice. Thus, the response signal can also be utilized to determine this direction. During the registration, a relative orientation of the microdevice at the location of the microdevice can be determined in some embodiments, thereby increasing the accuracy not only of the registration but also of the location determination of the microdevice in such embodiments.

In an example embodiment the registration apparatus further comprises an output interface configured to provide an output signal adapted to cause a visualization of a location of the microdevice in an ultrasound image based on the registration. For example, the location of the microdevice can be visualized by utilizing a virtual marker or other virtual highlighting that allows a user to perceive the determined location of the microdevice in the ultrasound image. Moreover, based on the known location of the microdevice and further based on a known relation between the microdevice and, for instance, the medical device, also a location of the medical device can be visualized in the ultrasound image.

Some embodiments the invention a reading system for reading a signal from a microdevice as described above and registering the reading system to an ultrasound system are presented, wherein the reading system comprises i) a field generator for generating a magnetic or electromagnetic excitation field for inducing a mechanical movement of a magnetic object of a magneto mechanical resonator of the microdevice, wherein the movement of the magnetic object generates a periodically changing response magnetic field, ii) a transducer for sensing and transducing the response magnetic field into an electrical response signal, iii) an apparatus as described above.

Generally, the field generator can refer to a field generator that can generate a periodically changing magnetic or electromagnetic field of a predetermined frequency. The transducer can refer to one or more magnetic coils that allow to transduce a magnetic field into an electric current that can be regarded as the electrical response signal. The processor is adapted to determine a location and/or a physical parameter and/or a change of a physical parameter in an environment of the microdevice based on the electrical response signals. In an example, the field generator comprises at least one air-core coil that is adapted to generate an excitation field between 1 kHz and 200 kHz, wherein the transducer is adapted to sense and transduce a magnetic signal of up to more than twice the frequency of the excitation field. In some embodiments, the transducer comprises at least one or beneficially more than three, air-core coils made from copper or aluminum.

Some embodiments of the invention a computer implemented registration method for registering an ultrasound system with an electromagnetic reading system for reading a signal from a microdevice as described above are presented, wherein the method comprises i) receiving a signal indicative of a transmit direction of an external ultrasound signal transmitted by the ultrasound system, ii) receiving an electrical response signal of the microdevice provided by the microdevice in response to a magnetic or electromagnetic excitation field provided by the electromagnetic reading system, iii) registering the ultrasound system with the reading system based on the electrical response signal and the transmit direction.

In an example embodiment the registration method as described above, further comprises determining a presence or absence of an external ultrasound signal at the microdevice based on the electrical response signal and a location of the microdevice relative to the electromagnetic reading system based on the electrical response signals, and registering the ultrasound system with the reading system based on a transmit direction of the external ultrasound signal, the determined location and the determined presence or absence of the external ultrasound signal. Moreover, the method further comprises determining a distance between the source of the ultrasound signal provided by the ultrasound system and the microdevice based on the electrical response signals, and registering the ultrasound system with the reading system further based on the determined distance. The registration method as described above, further comprising providing an output signal adapted to cause a visualization of a location of the microdevice in an ultrasound image based on the registration.

Some embodiments a computer program for causing the registration apparatus as described above to perform the method as described above are presented, when the computer program is included in instructions executable by a processor included in the registration apparatus.

These and other aspects of embodiments will be apparent from and elucidated with reference to the embodiments described hereinafter.

DETAILED DESCRIPTION

Figure 1:
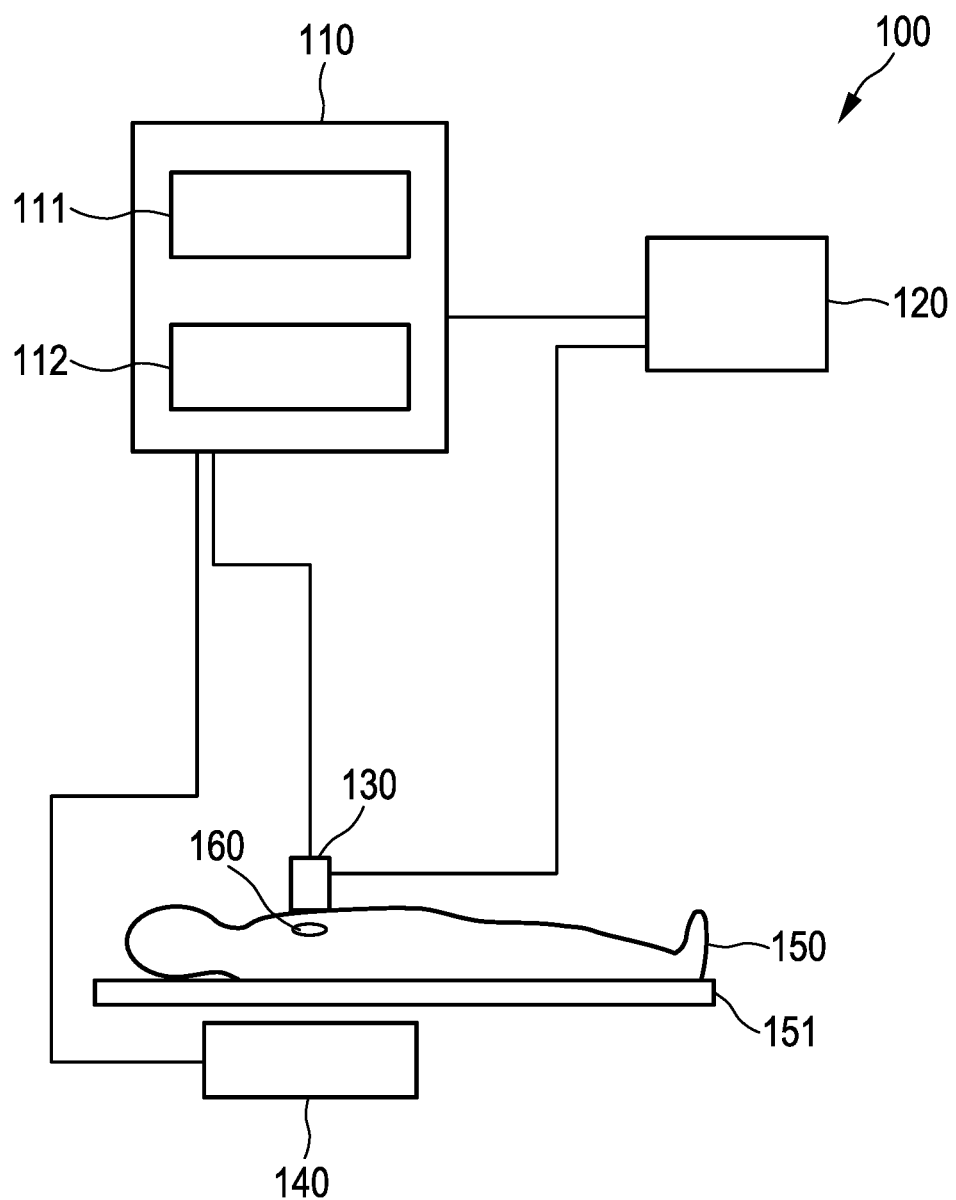
FIG. 1 shows an embodiment of a medical system comprising a microdevice and an apparatus for registering an ultrasound system and a reading system of a microdevice.

FIG. 1 shows schematically and exemplarily an embodiment of a medical system comprising a microdevice. The medical system 100 comprises an ultrasound system 130, a microdevice 160, and an electromagnetic reading system 140 for reading out the microdevice. Further, the medical system 100 comprises an apparatus 110 for registering the ultrasound system 130 and the electromagnetic reading system 140 and further an display 120 for providing an ultrasound image to the user indicating the position of the microdevice 160 in the ultrasound image.

Figure 3:
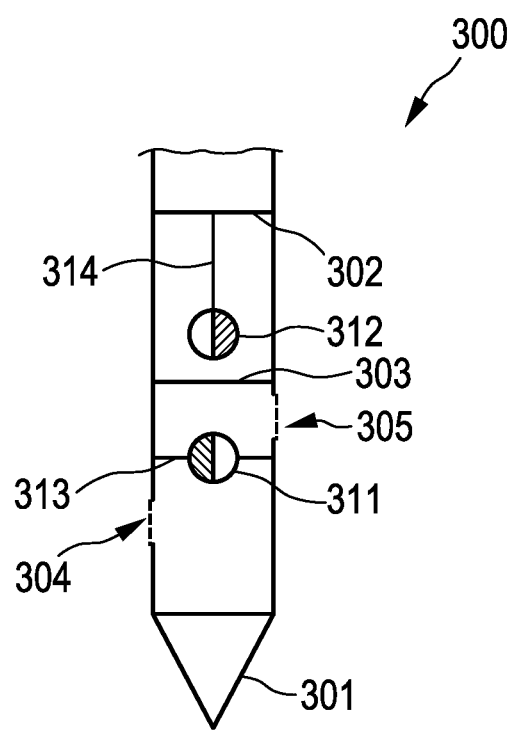
FIG. 3 shows an embodiment of a microdevice integrated into a medical tool.

In this, exemplarily embodiment a microdevice 160 is placed within a patient 150 placed on a patient table 151. The microdevice 160 is generally placed in a region of interest, i.e. in a region in which, for example, a surgical intervention should be performed. The microdevice 160 can be provided as, integrated in or attached to a medical tool that should be used in the region of interest. An example of a microdevice integrated into a medical tool is shown in FIG. 3. The medical tool 300 comprising the integrated microdevice is in this case realized in form of a medical needle with a tapered end 301. However, the medical tool 300 can generally be realized in any other form, for instance, as a catheter, guidewire, ablation element, etc. In the example shown in FIG. 3 the microdevice is directly integrated into the medical tool 300 such that a part of the casing is a part of a wall, for instance, an outer wall, of the medical tool 300. However, in other embodiments, the microdevice can also be provided with a casing that is not integrated into a housing of the medical tool and can for instance then be attached to a part of the microdevice. Within the casing 302 the microdevice comprises a magneto mechanical resonator that comprises in this example two magnetic objects 312, 311. The two magnetic objects 312, 311 are realized as magnetic spheres and are arranged within the casing 302 such that the magnetic poles of the two magnetic objects 312, 311 are in anti-parallel configuration, i.e. the positive pole of the magnetic object 312 faces the negative pole of the magnetic object 311. This configuration provides a restoring force acting on a magnetic object if it leaves its position. Generally, in this example the magnetic objects 312, 311 are shown as spheres, however, the magnetic objects can also be realized in other shapes, for example, as cylinders, ellipsoids, or any other shape that allows to provide a configuration in which the two magnetic objects 312, 311 provide a restoring force if one magnetic object is moved. In this example, the magnetic object 312 is attached to the casing 302 using a filament 314 that allows the magnetic object 312 to rotate around an axis formed by the filament 314. Since a rotation of the magnetic object 312 with respect to the magnetic object 311 causes a restoring force to act on the magnetic object 312, a movement of the magnetic object 311 will lead to a periodic movement around the neutral position shown in FIG. 3 and thus will lead to the generation of an electromagnetic field. Accordingly, by providing an external magnetic or electromagnetic excitation field to the microdevice that induces a rotation in the magnetic object 312 a periodically changing magnetic response field is generated.

In this embodiment of the microdevice the magnetic object 311 is attached to a pressure sensor 313 realized as a flexible membrane. In other embodiments, the pressure sensor may include another pressure sensor. In the embodiment shown in FIG. 3 the magnetic object 311 is integrated into the flexible membrane 313, however, the magnetic object could also be simply attached to the flexible membrane. Generally, the flexible membrane 313 comprises a flexibility that allows the flexible membrane 313 to react to a pressure difference on both sides of the flexible membrane 313, in particular, by moving in the direction with a lower pressure. Thus, a pressure induced movement of the magnetic object 311 will cause a distance change between the two magnetic objects 311, 312 and thus lead to a difference in the restoring force acting on the rotating magnetic object 312. Due to the change in the restoring force also the movement, in particular, the frequency of the rotational movement, of the magnetic object 312 will change leading to a change in the periodically changing magnetic response field. In particular, for this application of the microdevice the flexible membrane 313 is arranged such that a pressure difference induced by an external ultrasound signal will cause the movement of the flexible membrane 313. In some embodiments, the flexible membrane 313 is ultrasound sensitive by reacting to the quadratic terms of the pressure field, i.e. to the pushing force induced by an absorbed or reflected ultrasound energy and generally referring to the acoustic radiation pressure of the ultrasound signal.

Generally, the acoustic radiation pressure acting on an object can be calculated according to P=I/c, wherein P is a pressure, I is the incident power density, i.e. an incident power per unit area, of the incident radiation and c is the radiation velocity. For a generally known ultrasound transducer used in medical applications under an average distance between the region of interest and the transducer a good estimate for the incident power density is I≅15 kW/m$^2$ and the velocity can be estimated as c≅1500 m/s. From this estimate it follows that the acoustic radiation pressure of an ultrasound transducer in a medical application can be estimated as P≅0.1 mbar. Thus, a flexible membrane reacts with a movement of the magnetic object for pressure differences beneficially below 0.05 mbar, even more beneficially, below 0.01 mbar. For example, the flexible membrane can be made of a rubbery material like a silicone or latex and the signals of the flexible membrane can then be adjusted in order to allow for the reaction to the respective pressure difference.

In order to allow the pressure difference induced by the ultrasound signal to induce a movement of a flexible membrane, the pressure has to be transmitted through the casing 302 to the pressure sensitive flexible membrane 313. In this exemplary embodiment this is realized by providing openings 304, 305 in the casing of a microdevice. The openings 304, 305 are provided such that the interior of the casing 302 surrounding the magnetic object 311 is in a fluidic contact with a surroundings of the casing 302. For example, the openings 304, 305, can be directly open. However, in some embodiments, in order to avoid bodily fluids from entering the microdevice, the openings 304, 305 are closed, for example, with a flexible membrane that allows to transmit a pressure from the outside of the casing 302 to the inside of the part of the casing 302 surrounding the magnetic object 311. Moreover, in this exemplarily embodiment the two medical objects 311,312 are separated by a separator 303. Accordingly, the pressure transmitted into the casing 302 can only act on the pressure sensitive membrane 313 and thus only on magnetic object 311, while the filament 314 and the magnetic object 312 will not be influenced by any pressure differences. This allows for an easier calibration of the microdevice and a more accurate measurement of the pressure difference induced by the ultrasound signal.

The microdevice described above can for instance be utilized as a microdevice 160 shown in FIG. 1. The ultrasound system 130 can refer to any known medical ultrasound system and comprises an ultrasound transducer that provides ultrasound signals into a region of interest in the patient in which the microdevice 160 is positioned. Generally, the ultrasound system 130 provides ultrasound signals in form of pencil beams, fan beams, or cone beams, wherein based on the position of the ultrasound system 130 a direction of a currently emitted ultrasound signal relative, for instance, to the region of interest, the position of the ultrasound device 130 or any other fixed position that can define a coordinate system, can be determined. The ultrasound system 130 is then configured to provide a signal to the apparatus that is indicative of a current direction in which the ultrasound signal is provided by the ultrasound transducer.

The system further comprises the electromagnetic reading system 140 for reading out the microdevice. The reading system 140 comprises at least a field generator for generating the magnetic or electromagnetic excitation field that can be used to excite the microdevice 160. Further, the reading system 140 comprises one or more transducers that can measure the generated response magnetic field of the microdevice and transduce the generated response magnetic field into an electrical response signal. In some embodiments, the field generator can also be utilized as transducer in addition or alternatively to the other transducers described above. The transducers can be realized as coils transducing the response magnetic field generated by the microdevice 160 into an electrical response signal. The electrical response signal can then be provided to a processor that is adapted to process the electrical response signals, for instance, for localizing the microdevice 160 or for determining a physical parameter measured by the microdevice in its environment. In particular, the processor can be adapted to compare the response signal of different transducers and based on this comparison use a triangulation algorithm to determine the location of the microdevice. Moreover, the processor can be adapted to analyze a frequency spectrum of the response signal and to compare the frequency spectrum to a frequency spectrum that is stored already, for instance, from a previous time span or from a calibration measurement. Based on this comparison the processor can then determine a physical parameter or a change in a physical parameter in the environment of the microdevice. However, also other methods can be utilized for localizing the microdevice and/or for determining a physical parameter based on the response signals.

Moreover, the processor can determine based on the response signal generated by the microdevice the presence of an ultrasound signal. For example, in a previous calibration procedure the signals changes caused by an ultrasound signal meeting the microdevice 160 at different angles and at different distances can be recorded and the respective response signals can be compared to current response signals of the microdevice. Based on the comparison it can be determined when an ultrasound signal reaches the microdevice. Moreover, if the microdevice 160 is further configured such that the flexible membrane reacts differently to different directions under which the ultrasound signal meets the microdevice, also this direction can be determined by the processor based on the response signal provided by the microdevice 160. Moreover, since the radiation pressure of the ultrasound signal provided to the microdevice depends on the distance between the microdevice 160 and the ultrasound transducer 130, also this distance can be determined, for example, by the processor, based on the electromagnetic response signal of the microdevice 160. Generally, the intensity of an ultrasound beam changes with distance in a known way. For example, for a point source, it decreases with the square of the distance, if there is negligible absorption. However, in reality, the situation can be more complicated, if the ultrasound field is shaped by the ultrasound transducer and does not refer to a simple point source. However, the shape of the ultrasound beam is generally known and can be provided, for example, based on a specification or based on calibration measurements for an ultrasound system. Based on this knowledge the distance from the ultrasound transducer to the microdevice can be calculated. The accuracy of the distance calculation can further be increased if the attenuation and diffraction/scattering of the ultrasound signal by the tissue is taken into account. For example, a respective estimation for common soft tissues can be found in literature for a specific ultrasound frequency and tissue type. Based on the attenuation and diffraction/scattering estimate and based on the shape of the ultrasound beam for a given ultrasound probe, a relative accurate prediction, i.e. theoretical intensity, for the ultrasound intensity over depth, i.e. distance, can be derived. As the microdevice measures the ultrasound intensity, it is possible to reconstruct the depth, i.e. distance, by comparing the measured intensity with the theoretical intensity and determining the distance based on the comparison, e.g. by selecting the distance that matches best. Furthermore, to further increase the accuracy, a dependency of the measured intensity by the microdevice on the orientation of the microdevice relative to the angle of the ultrasound field can be taken into account. This angle can be determined, for example, from a known position of the microdevice relative to the reading system and a position of an additional marker attached to the ultrasound probe. However, also other possibilities for determining a position of the ultrasound probe in a coordinate system of the reading system can be utilized, for example, touching the microdevice to the ultrasound device, etc.

If the reading system does not comprise a processor in itself it can directly provide the electromagnetic response signal received from the microdevice 160 to the apparatus 110 and the processor 112 of the apparatus 110 can determine the location of the microdevice and optionally also the distance between the microdevice and the ultrasound transducer and/or the direction from which the ultrasound signal meets the microdevice 160 based on the electromagnetic response signal provided by the reading system 140. However, if the reading system 140 comprises a processor that can calculate this measures, the reading system 140 can provide a signal to the apparatus 110 that is indicative of the already calculated measures. In this case it can be regarded that the processor 112 of the apparatus 110 and the processor of the reading system 140 perform the function of registering the ultrasound system and the reading system 130, 140 together in a distributed computing.

The apparatus 110 registers the ultrasound system 130 with the electromagnetic reading system 140. In particular, a registration of the two systems refers to determining a function that allows to calculate based on the location of the microdevice determined by the reading system 140 the location of the microdevice 160 in the ultrasound image of the ultrasound system 130. In particular, this function refers to a coordinate transformation that transforms the coordinates of the location of the microdevice 160 in the coordinate system of the reading system 140 to the coordinate system of the ultrasound image, i.e. to the coordinate system of the ultrasound system 130. For this the registration apparatus 110 comprises a receiving interface 111 that can be realized as any form of communicative interface that allows to receive wired or wireless signals from the ultrasound system 130 and the reading system 140. Accordingly, the receiving interface can receive a signal from the ultrasound system that is indicative of the direction of the ultrasound signal. For example, the signal can be indicative of a current direction of the ultrasound signal or can comprise a sequence of directions of the ultrasound signal associated with the respective time at which the ultrasound signal is provided in the respective direction. Further, the receiver can receive accordingly from the reading system 140, as described above, a response signal of the microdevice 160 or directly the determined location of the microdevice and optionally also the distance between the microdevice and the ultrasound transducer and/or a direction under which the ultrasound signal meets the microdevice 160. Moreover, the signal received by the receiving interface can also be indicative when the ultrasound signal meets the microdevice 160. For example, the signal can be indicative whether or not currently the microdevice 160 is subject to an ultrasound signal, and/or can be indicative of the times at which the microdevice was subject to the ultrasound signal. However, as also described above, the receiving interface 111 can also receive a signal that is indicative of the electrical response signal of a microdevice, wherein in this case the processor 112 executes instructions to determine the above measures.

The processor 112 registers the ultrasound system with the reading system based on the response signal, in particular, based on the measures derived from the response signal and the transmit direction. In particular, in a first step the processor determines times at which the microdevice 160 is subjected to the ultrasound signal. The processor can then utilize the transmit direction of the ultrasound signal from these times since at these times the position of the microdevice lies within the region covered by the ultrasound signal transduced in the transmit direction. Further, the processor utilizes the location of the microdevice 160 determined based on the response signal to determine the registration. In particular, based on the location and the direction of the ultrasound signal a registration in at least one direction, if the ultrasound signal is a pencil beam also in two directions, can be performed. A registration in all three directions can be based on further information. For example, during a calibration procedure the microdevice can be placed in a predetermined distance from the ultrasound transducer and can then be placed in different locations in order to register all three directions. However, if during the interventional procedure the response signal also provides information about the distance to the ultrasound transducer and/or the direction under which the ultrasound signal meets the microdevice 160, the calibration procedure can be omitted, and the directly derived information during the interventional procedure can be utilized for registering the ultrasound system and the reading system in all three directions.

Figure 4:
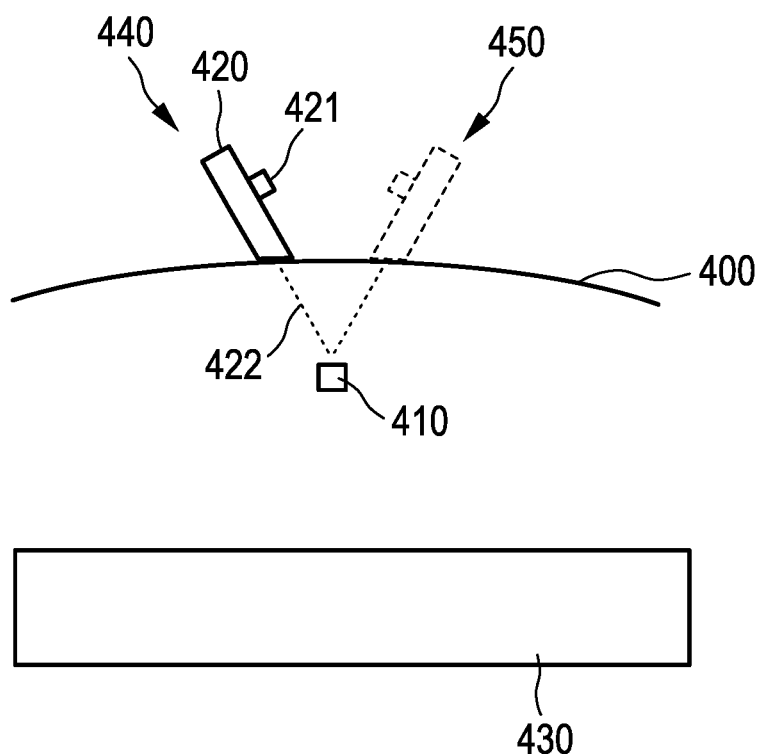
FIG. 4 shows an embodiment of a calibration procedure for registering the ultrasound system and the reading system.

A calibration procedure that can be utilized for determining the registration is described in the following based on FIG. 4. In this embodiment, the ultrasound system 420 comprises an additional marker 421 that allows to determine the location of the ultrasound system in the coordinate system of the reading system. The additional marker can be any device that provides a signal measurable by the reading system. For example, the marker can comprise an LC resonator that responds to the changing electromagnetic field provided by the reading system and generates a respective response signal that can be measured by the reading system. However, the marker can also be an active marker that generates an electromagnetic signal measurable by the reading system independent of an external magnetic or electromagnetic field. Beneficially the marker is realized as a microdevice comprising a magneto mechanical resonator similar to the magneto mechanical resonator of the microdevice. However, the magneto mechanical resonator is beneficially only adapted for allowing a localizing of the additional marker without providing an ultrasound detectability. Beneficially, the ultrasound system, in particular the ultrasound probe 420, can be equipped with an additional marker capable to be localized in 6 degrees of freedom relative to the reading system. When the position and optionally orientation of the microdevice and additional marker are known and if further the position and beam angle of the ultrasound system is known, generally a microdevice position can be computed relative to the ultrasound image. This allows for a position indication of the microdevice in an ultrasound image without determining the absence or presence of the ultrasound signal at the location of the microdevice. However, the position and orientation of the microdevice relative to the additional marker can often not be determined with sufficient precision or can change during an interventional procedure due to changes in the electromagnetic field used for determining the positions of the microdevice and the marker. For example, metallic objects near a patient can disturb the electromagnetic field and it might not always be possible to ensure that a position of the object and thus the disturbance does not change during the interventional procedure. In these cases, it is advantageous if a fast and easy way can be provided that allows to again determine the position of the microdevice in the ultrasound image very accurately. Therefore, it is beneficial to register the ultrasound system and the reading system in a fast and easy calibration procedure that can be repeated, if necessary during an interventional procedure. In an exemplary calibration procedure, the user positions the ultrasound probe 420 with the additional marker 421 relative to the microdevice 410, for instance, on a surface 400 of the patient or a calibration dummy. The ultrasound beam 422 can then be angled in a way that the microdevice 410 detects the ultrasound signal. The detection of the ultrasound signal at the first position 440 together with the information on the locations of the microdevice 410, the additional marker 421 and the angle, i.e. direction, of the ultrasound beam 422 can then be stored. This procedure can then be repeated at least two times at different positions of the ultrasound probe 420, for example, the same information can also be determined for a second position 450 of the ultrasound probe 420. The registration processor optimizes the beam starting point, or line for an array transducer, position and the beam angle or beam plane angle for a 2D array, relative to the additional marker in the coordinate system of the reading system 430 to fit all the measurements. The optimization then results in a registration that allows to display the position of the microdevice in the ultrasound image, based on the microdevice position and the additional marker position. Moreover, if the ultrasound probe is not moved during the interventional procedure the registration allows even to only use the microdevice position for determining and displaying the microdevice in the ultrasound image.

Based on the registration the location of the microdevice 116 in the ultrasound image 120 provided by the ultrasound system 130 can be determined utilizing the location of the microdevice 160 as determined by the reading system 140. Thus, the apparatus 110 can utilize the registration result to determine the location of the microdevice 160 in the ultrasound image and provide this location to a display 120. Further, the ultrasound system 130 can provide the ultrasound image to the display 120 and the display 120 can then display the ultrasound image showing the location of the microdevice 160. In particular, a marker or other virtual representation of the microdevice can indicate the location of the microdevice in the ultrasound image and thus in the region of interest. Since in most cases the microdevice will be provided as integrated into or attached to a medical device, based on the location of the microdevice 160 also the location of the medical device can be indicated in the ultrasound image 120, for instance, by using a virtual representation of the medical device.

Figure 2:
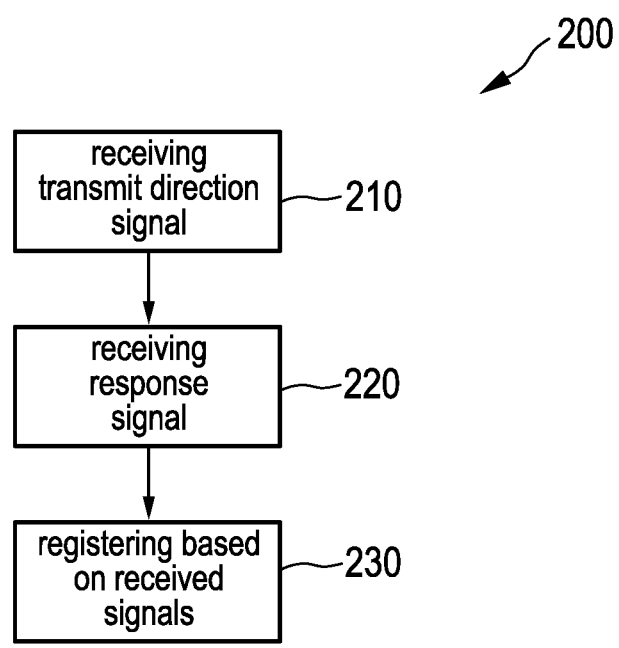
FIG. 2 shows an embodiment of a method for registering an ultrasound system and a reading system of a microdevice.

FIG. 2 shows schematically and exemplarily a flow chart of the method 200 for registering the ultrasound system with the reading system for a microdevice. The method 200 comprises a step 210 of receiving a signal indicative of the transmit direction of the ultrasound signal transmitted by the ultrasound system, for instance, ultrasound system 130. Further, the method comprises a step 220 of receiving a signal indicative of the response signal of the microdevice, for example, as provided by the reading system 140. Further, the method 200 comprises a step 230 of registering the ultrasound system with the reading system based on the electrical response signal and the transmit direction, for example, as already described above with respect to the apparatus 110 in detail.

Although in the above embodiments the microdevice was integrated into a medical tool, in other embodiments the microdevice can also be provided with its own casing and can then be attached to a medical tool or can be provided, for instance, as marker, in a region of interest without a medical tool.

Although in the above embodiments the microdevice was provided with the magnetic object attached to a filament in a magnetic object attached to a flexible membrane, in other embodiments both medical objects might be attached to flexible mem-branes, or to filaments. Moreover, also other attachments can be utilized like springs flexible filaments, etc.

Moreover, although in the above embodiments the response signal was provided by the magnetic objects due to a rotation of the magnetic objects in other embodiments the response signal can also be provided by other movements of the magnetic objects relative to each other, for instance, by movements periodically changing a distance between the magnetic objects or changing an orientation of the magnetic objects. Furthermore, although in the above embodiments the pressure sensor was provided as a flexible membrane, in other embodiments the pressure sensor can refer to or include any pressure sensor that allows introduction of a relative motion between the magnetic objects. For example, a pressure sensitive spring or filament or any other construction can also be utilized, too, or instead.

Although in the above embodiments the microdevice was provided with two magnetic objects, in other embodiments the microdevice can also be provided with more than two magnetic objects, for instance, also magnetic objects in between the two magnetic objects can be provided or at the sides of the magnetic objects in order to stabilize the movement of the magnetic objects. Furthermore, although in the above embodiments the casing was provided with two openings, in other embodiments the openings can be omitted, for example, if the casing itself is provided with a flexible material, or more than two openings can be provided. In some embodiments, four openings are provided in order to allow for an accurate pressure transmitting between the outside of the casing and the inside of the casing.

In some embodiments, the memory can include any one or combination of volatile memory elements (e.g., random access memory (RAM, such as DRAM, SRAM, SDRAM, etc.) and nonvolatile memory elements (e.g., ROM, hard drive, Flash, EPROM, EEPROM, CDROM, etc.). Moreover, the memory may incorporate electronic, magnetic, optical, semi-conductive, and/or other types of storage media.

In some embodiments, the processor is a hardware device (including a processing circuit) for executing software, particularly that stored in memory. The processor may be included in a server. The processor can be any custom made or commercially available processor, a central processing unit (CPU), an ASIC, a GPU, a semiconductor based processor (e.g., in the form of a microchip or chip set), a macroprocessor, a controller, a microcontroller or generally any device for executing program or software instructions.

A computer program or software can be stored on any non-transitory computer readable medium for use by or in connection with any computer related system or method. In the context of this document, a computer readable medium comprises an electronic, magnetic, optical, electromagnetic, infrared, or semiconductor system, apparatus, device or means that can contain or store a computer program for use by or in connection with a processor, processing circuit, computer related system or method. The software can be embodied in any non-transitory computer-readable medium for use by or in connection with an instruction execution system, apparatus, or device, such as a computer-based system, processor-containing system, or other system that can fetch the instructions from the instruction execution system, apparatus, or device and execute the instructions. A computer program may be stored/distributed on a suitable medium, such as an optical storage medium or a solid-state medium, supplied together with or as part of other hardware, but may also be distributed in other forms, such as via the Internet or other wired or wireless telecommunication systems.

The display can include a display screen or other output unit. The display may be embodied in one or more of several technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), etc. Other variations to the disclosed embodiments can be understood and effected by those skilled in the art from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the receiving of the signals, the registering of the systems, et cetera, performed by one or several units or devices can be performed by any other number of units or devices. These procedures can be implemented as program code of a computer program and/or as dedicated hardware.

Any reference numbers in the claims should not be construed as limiting the scope.

The invention claimed is:

1. A microdevice, comprising:
   a casing;
   a magneto mechanical resonator disposed within the casing, wherein the magneto mechanical resonator comprises:
      at least two magnetic objects,
         wherein the at least two magnetic objects are arranged to provide a permanent magnetic moment,
      wherein the magneto mechanical resonator is arranged to transduce an external magnetic or electromagnetic excitation field into a mechanical movement of the at least two magnetic objects relative to each other,
      wherein the mechanical movement of the at least two magnetic objects relative to each other is configured to produce a periodically changing magnetic response field, and
   a pressure sensitive element,
      wherein the pressure sensitive element is arranged to induce an additional movement of a first one of the at least two magnetic objects relative to a second one of the at least two magnetic objects in response to an external ultrasound signal, wherein the external ultrasound signal is applied externally to the microdevice, and
      wherein the additional movement of the first one of the at least two magnetic objects relative to the second one of the at least two magnetic objects in response to the external ultrasound signal is configured to change the periodically changing magnetic response field.

2. The microdevice of claim 1, wherein the pressure sensitive element comprises a flexible membrane, and wherein one of the at least two magnetic objects is attached to the flexible membrane, wherein a movement of the flexible membrane is configured to cause the additional movement of the first one of the at least two magnetic objects relative to the second one of the at least two magnetic objects.

3. The microdevice of claim 1, further comprising a separator disposed within the casing, wherein the separator is configured to separate a first region within the casing from a second region within the casing, wherein the first one of the at least two magnetic objects and the pressure sensitive element are disposed within the first region and the second one of the at least two magnetic objects is disposed within the second region, wherein the first one of the at least two magnetic objects and the pressure sensitive element disposed within the first region are arranged to be exposed to the external ultrasound signal, and the second one of the at least two magnetic objects is disposed within the second region is arranged to not be exposed to the external ultrasound signal.

4. The microdevice of claim 1, wherein the pressure sensitive element is disposed within the casing.

5. The microdevice of claim 1, wherein the periodically changing magnetic response field indicates a direction from which the external ultrasound signal reaches the microdevice.

6. The microdevice of claim 1, wherein the additional movement of the first one of the at least two magnetic objects relative to the second one of the at least two magnetic objects in response to the external ultrasound signal is configured to change a frequency of the periodically changing magnetic response field.

7. The microdevice of claim 1, wherein the pressure sensitive element and the first one of the at least two magnetic objects are arranged such that a frequency of the additional movement induced by the external ultrasound signal is less than a frequency of the external ultrasound signal.

8. The microdevice of claim 1, wherein the casing and the pressure sensitive element are arranged to produce a pressure difference between different areas within the casing in response to the external ultrasound signal, wherein the pressure sensitive element is arranged to cause the additional movement of the first one of the at least two magnetic objects relative to the second one of the at least two magnetic objects in response to the pressure difference produced in response to the external ultrasound signal.

9. The microdevice of claim 8, further comprising a separator disposed within the casing, wherein the separator is configured to separate a first region within the casing from a second region within the casing, wherein the first one of the at least two magnetic objects is disposed within the first region and the second one of the at least two magnetic objects is disposed within the second region, wherein the pressure difference exists within the first region and does not exist within the second region in response to the external ultrasound signal.

10. The microdevice of claim 8, wherein the pressure sensitive element is disposed within the casing.

11. The microdevice of claim 8, wherein the casing comprises at least two openings, wherein the pressure sensitive element is arranged between the at least two openings, wherein the pressure sensitive element is configured to experience the pressure difference at two opposing sides thereof in response to the external ultrasound signal.

12. The microdevice of claim 11, further comprising at least one flexible membrane covering at least one of the at least two openings, wherein the at least one flexible membrane is arranged to transmit a pressure, produced by the external ultrasound signal, from outside of the casing to inside of the casing.

13. The microdevice of claim 11, wherein the pressure sensitive element is disposed within the casing.

14. The microdevice of claim 11, further comprising a separator disposed within the casing, wherein the separator is configured to separate a first region within the casing from a second region within the casing, wherein the first one of the at least two magnetic objects is disposed within the first region and the second one of the at least two magnetic objects is disposed within the second region, wherein the pressure difference exists within the first region and does not exist within the second region in response to the external ultrasound signal.

15. The microdevice of claim 14, wherein the pressure sensitive element is disposed within the first region.

16. The microdevice of claim 14, further comprising at least one flexible membrane covering at least one of the at least two openings, wherein the at least one flexible membrane is arranged to transmit a pressure, produced by the external ultrasound signal, from outside of the casing to the first region within the casing but not to the second region within the casing.

17. The microdevice of claim 16, wherein the pressure sensitive element is disposed within the first region.

* * * * *